United States Patent
Martin et al.

(10) Patent No.: US 7,291,310 B2
(45) Date of Patent: Nov. 6, 2007

(54) MICROSYSTEM FOR DETERMINING CLOTTING TIME OF BLOOD AND LOW-COST, SINGLE-USE DEVICE FOR USE THEREIN

(75) Inventors: Steven M. Martin, Ann Arbor, MI (US); Roy H. Olsson, III, Ann Arbor, MI (US); Richard B. Brown, Ann Arbor, MI (US); Robert K. Franklin, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 818 days.

(21) Appl. No.: 10/737,422

(22) Filed: Dec. 16, 2003

(65) Prior Publication Data
US 2004/0147032 A1 Jul. 29, 2004

Related U.S. Application Data

(60) Provisional application No. 60/434,186, filed on Dec. 17, 2002.

(51) Int. Cl.
*G01N 33/86* (2006.01)
*G01N 27/02* (2006.01)

(52) U.S. Cl. .................. 422/73; 422/68.1; 422/100; 436/63; 436/69; 436/149; 436/150; 436/151; 436/180; 600/369; 73/64.41

(58) Field of Classification Search ............... 436/63, 436/69, 73, 74, 80, 84, 149, 150, 151, 180; 422/68.1, 73, 100; 600/369; 73/64.41
See application file for complete search history.

(56) References Cited

U.S. PATENT DOCUMENTS

| 3,699,437 | A | * | 10/1972 | Ur ............................. 324/722 |
| 3,840,806 | A | * | 10/1974 | Stoner et al. ............... 324/722 |
| 4,105,411 | A | | 8/1978 | Biver |
| 4,125,327 | A | | 11/1978 | Margolis |
| 4,301,414 | A | * | 11/1981 | Hill et al. ................... 324/446 |
| 4,797,369 | A | | 1/1989 | Mintz |
| 4,876,069 | A | | 10/1989 | Jochimsen |
| 4,964,728 | A | | 10/1990 | Kloth et al. |
| 5,039,617 | A | | 8/1991 | McDonald et al. |
| 5,167,145 | A | | 12/1992 | Butler et al. |

(Continued)

FOREIGN PATENT DOCUMENTS

WO   99/47907   *   9/1999

(Continued)

OTHER PUBLICATIONS

Martin et al. Proceedings of the 39th Annual Design Automation Conference (DAC), vol. CONF 39, pp. 1-7, Jun. 10-14, 2002.*

(Continued)

*Primary Examiner*—Maureen M. Wallenhorst
(74) *Attorney, Agent, or Firm*—Brooks Kushman P.C.

(57) ABSTRACT

A microsystem for determining clotting time of blood and a low-cost, single-use device for use therein are provided wherein the device has no moving parts or expensive optical sensors or magnets. The device includes a microfluidic channel and a microsensor at least partially in fluid communication with the channel. By analyzing changes in the sensor as a drop of blood flows down the microfluidic channel, the time at which the blood clots can be determined.

23 Claims, 6 Drawing Sheets

U.S. PATENT DOCUMENTS

| | | | |
|---|---|---|---|
| 5,491,408 A * | 2/1996 | Rousseau | 324/71.1 |
| 5,504,011 A | 4/1996 | Gavin et al. | |
| 5,601,995 A * | 2/1997 | Exner | 435/13 |
| 5,628,961 A * | 5/1997 | Davis et al. | 422/63 |
| 5,908,786 A | 6/1999 | Moreno et al. | |
| 6,066,504 A | 5/2000 | Jina | |
| 6,150,174 A * | 11/2000 | Sin et al. | 436/69 |
| 6,437,551 B1 * | 8/2002 | Krulevitch et al. | 324/71.1 |
| 6,438,498 B1 | 8/2002 | Opalsky et al. | |
| 6,448,024 B1 | 9/2002 | Bruegger | |
| 6,521,182 B1 | 2/2003 | Shartle et al. | |
| 6,555,064 B2 | 4/2003 | Baugh et al. | |
| 6,766,817 B2 | 7/2004 | da Silva | |
| 7,021,122 B1 * | 4/2006 | Rosemberg et al. | 73/54.01 |

FOREIGN PATENT DOCUMENTS

| | | | |
|---|---|---|---|
| WO | 02/050534 | * | 6/2002 |
| WO | 2004/059316 | * | 7/2004 |

OTHER PUBLICATIONS

Carville, D.G., et al., "Coagulation Testing Part 2: The Quest to Optimize Near-Patient Analyzers," IVD Technology Magazine, Sep. 1998, pp. 1-10.

Seegers, Walter Ed., "Blood Clotting Enzymology," Academic Press, New York, NY 1967, pp. 1-21.

Wintrobe, Maxwell M., Ed., "Blood, Pure and Eloquent," McGraw-Hill Book Co., New York, NY, 1980, Chapter 18, pp. 601-656.

Dailey, John F., "Blood," Medical Consulting Group, Arlington, MA, 1998, Chapter 12, pp. 190-209.

Albrittion, E.C., Ed., "Standard Values in Blood," W.B. Sanders Co., Philadelphia, PA, 1952, Chapter 13, pp. 15-16.

Schmer, Gottfried, et al., Eds., "Coagulation Current Research and Clinical Applications," Chapter on Modern Concept of Blood Coagulation, Academic Press, New York, NY, 1973, pp. 3-15.

Blair, G.W. Scott, et al., "An Introduction to Biorheology," Elsevier Scientific Publishing Co., New York, NY, 1974, Chapter VI, pp. 62-83.

Kaibara, M., "Rheological Studies on Blood Coagulation and Network Formation of Fibrin," Polymer, Gel, and Networks, vol. 2, No. 1, 1994, pp. 1-28.

Hrncir, E., et al., "Surface Tension of Blood," Physiological Research, vol. 46, No. 4, Aug. 1997, pp. 319-321.

Bard, A., et al., "Electrochemical Methods," John Wiley and Sons, New York, NY, 1980, pp. 6-8.

Blake, L.E., "Principles of the Impedance Technique," IEEE Eng. in Medicine and Biology Magazine, vol. 8, No. 1, Mar. 1989, pp. 11-15.

Olsson, R.H., III, et al., "Silicon Neural Recording Arrays with On-Chip Electronics for In-Vivo Data Acqusition," IEEE-EMBS Special Topic Conference on Microtechnologies in Medicine and Biology, pp. 237-240, Poster 114, May 2002.

Lorenz, H., et al., "High-Aspect Ratio, Ultrathick, Negative-Tone Near-UV Photoresist and its Applications for MEMS," Sensors and Actuators A: Physical, vol. 64, No. 1, Jan. 1998, pp. 33-39.

Nolan, Troy C., et al., Direct Down-Conversation of Passband Signals Using MEMS Filters and Sub-Sampling, IEEE, 1999, pp. 1896-1899.

Nelson, D.T., et al., High-Dynamic Range Chanelized MEMS Equalizing Filter, OFC 2002, ThCC3, pp. 586-588.

* cited by examiner

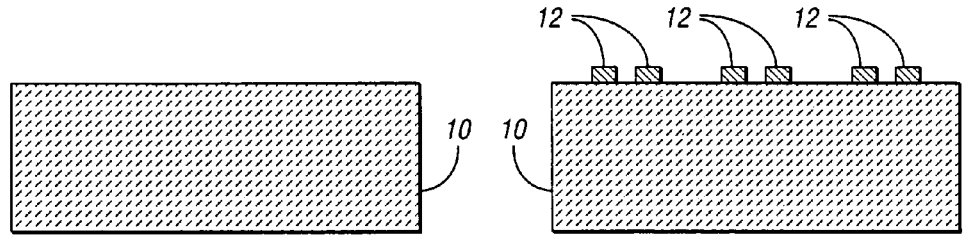
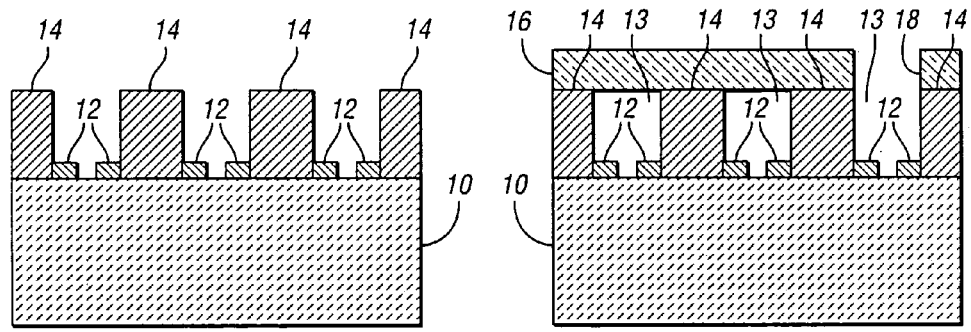
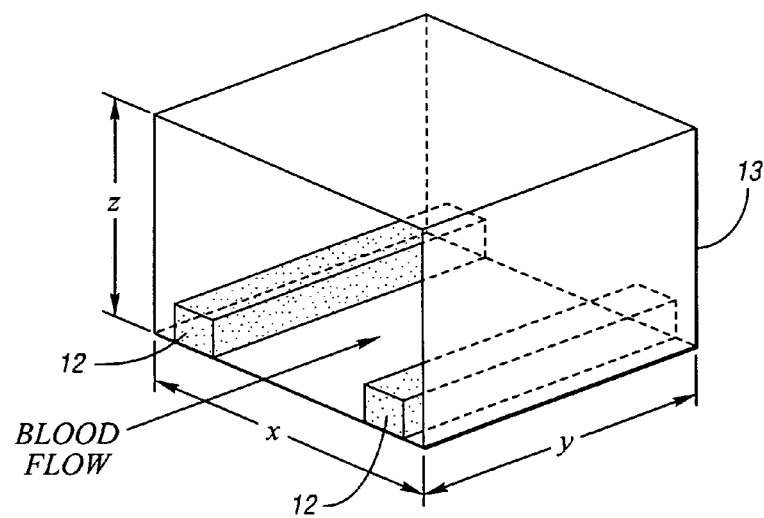

MICROSYSTEM FOR DETERMINING CLOTTING TIME OF BLOOD AND LOW-COST, SINGLE-USE DEVICE FOR USE THEREIN

CROSS-REFERENCE TO RELATED APPLICATION

This application claims the benefit of U.S. provisional application Ser. No. 60/434,186, filed Dec. 17, 2002 and entitled "Microsystem for Clotting Time Blood Tests."

BACKGROUND OF THE INVENTION

1. Field of the Invention

This application relates to Microsystems for determining clotting time of blood and low-cost, single-use devices for use therein.

2. Background Art

The following references are referred to herein:

[1] D. G. Carville et al., "Coagulation Testing Part 2: The Quest to Optimize Near-Patient Analyzers," IVD TECHNOLOGY MAGAZINE, September 1998.
[2] Walter Seegers ed., "Blood Clotting Enzymology," ACADEMIC PRESS, New York, N.Y. 1967.
[3] Maxwell M. Wintrobe ed., "Blood, Pure and Eloquent," MCGRAW-HILL BOOK CO., New York, N.Y. 1980.
[4] John F. Dailey, "Blood," MEDICAL CONSULTING GROUP, Arlington, Mass., 1998.
[5] E. C. Albrittion ed., "Standard Values in Blood," W. B. SANDERS CO., Philadelphia, Pa. 1952.
[6] Gottfried Schmer and Paul E. Strandijard, eds., "Coagulation Current Research and Clinical Applications," ACADEMIC PRESS, New York, N.Y. 1973.
[7] G. W. Scott Blair, "An Introduction to Biorheology," ELSEVIER SCIENTIFIC PUBLISHING CO., New York, N.Y. 1974.
[8] M. Kaibara, "Rheological Studies on Blood Coagulation and Network Formation of Fibrin," POLYMER, GEL, AND NETWORKS, Vol. 2, No. 1, 1994, pp. 1-28.
[9] E. Hrncir et al., "Surface Tension of Blood," PHYSIOLOGICAL RESEARCH, Vol. 46, No. 4, August 1997, pp. 319-321.
[10] A. Bard et al., "Electrochemical Methods," JOHN WILEY AND SONS, New York, N.Y. 1980.
[11] V. F. Rusyaev, "Conductive Method of Studying Blood Coagulation," BIOMEDICAL ENGINEERING, Vol. 21, No. 3, May-June 1987, pp. 114-118.
[12] L. E. Blake, "Principles of the Impedance Technique," IEEE ENG. IN MEDICINE AND BIOLOGY MAGAZINE, Vol. 8, No. 1, March 1989, pp. 11-15.
[13] R. H. Olsson III et al., "Silicon Neural Recording Arrays with On-Chip Electronics for In-Vivo Data Acquisition," IEEE-EMBS SPECIAL TOPIC CONFERENCE ON MICROTECHNOLOGIES IN MEDICINE AND BIOLOGY, pp. 237-240, May 2002.
[14] H. Lorenz et al., "High-Aspect Ratio, Ultrathick, Negative-Tone Near-UV Photoresist and its Applications for MEMS," SENSORS AND ACTUATORS A: PHYSICAL, Vol. 64, No. 1, January 1998, pp. 33-39.

In an effort to reduce health care costs, the medical industry has been moving away from centralized laboratories to point-of-care instrumentation and analysis. One such example is near-patient blood coagulation analyzers [1], including Technidyne Corp.'s Hemachron 8000 and Cardiovascular Dynamics Inc.'s TAS. Many different-diseases, including Hemophilia A and B, thrombocythmia, Christmas disease, and prothrombin deficiency, affect the in vivo coagulation of blood. Treatment of these diseases requires medication with either coagulants or anticoagulants like the industry standard heparin or tannin [2,3]. In order to ensure proper medication, at-home testing would be a great benefit for individuals suffering from these diseases. Near-patient blood testing during cardiac surgery is equally important because blood clotting must be monitored to ensure a successful operation. An accelerated clotting time (ACT) test is used in this situation to make sure the patient is properly heparinized [4].

Clearly there is a need for low-cost blood coagulation analyzers. Additionally, disposable, single-use devices are preferable so as to avoid autoclaving and other cleaning procedures.

Blood coagulation analysis is useful for determining proper medication for medical conditions such as hemophilia, liver disease, and cardiac surgeries and has many uses in laboratories, hospitals, and even at home.

The following is a brief list of some makers of blood coagulation analyzers, the product, name, and the detection scheme:

1. Helena Laboratories (http://www.helena.com) makes an instrument called the Actalyke. This device places a magnet in the blood and oscillates it back and forth detecting the rate of movement. The change in rate of movement detects coagulation.
2. i-STAT (http://www.istat.com) makes an instrument called the i-STAT. This device uses an indicator substance to detect hemocrit. This indicator is then sensed electrochemically.
3. Instrumentation Laboratories (http://www.ilus.com) makes an instrument called the GEM PCL. This device flows the blood past an optical window until the blood no longer passes indicating that it has clotted.
4. International Technidyne Corporation (http://www.itc-med.com) makes an instrument called the ProTime Microcoagulation System. This is intended to be an at-home test device. The coagulation is detected by pumping a precise amount of blood back and forth in a channel until it no longer flows.
5. Sienco, Inc. (http://www.uscid.org/~sienco/) has an instrument called Sonoclot. Sonoclot works by placing a mechanical probe into the blood and mechanically resonating it back and forth. By detecting the resistance to motion changes, a determination of the blood's coagulation can be determined.

The following are prior art U.S. patents related to blood clot sensors:

U.S. Pat. No. 5,039,617—McDonald et al describes capillary channels in plastic devices for measuring accelerated clotting time tests. Included in this patent are chambers for mixing the reagents needed for the ACT tests and methods for including the reagents. Optical or electromechanical techniques are used for detection of coagulation times.

U.S. Pat. No. 6,521,182—Shartle et al. A channel flow to a measurement area where optical transmittance is measured. A disposable cartridge-type device.

U.S. Pat. No. 5,504,011—Gavin et al. A channel-type device that requires pneumatic pumps to move fluid back and forth, thus recording its clotting time.

U.S. Pat. No. 5,908,786—Moreno et al. A long elongated channel with microheaters underneath. A thermionic compound is mixed with the blood and based on how far it flows into the channel, the color is changed and the results are read by the users like a litmus paper test.

U.S. Pat. No. 6,448,024 is an update of the McDonald et al. patent. The device is used to measure both clotting time and amount of fribrinogen by mixing in different compounds.

U.S. Pat. No. 4,797,369—Mintz. Blood is continuously brought together in a chamber and then separated. A fibrigen bridge is formed between the two solutions when clotting starts and this creates an electrical short between the two solutions.

Published U.S. patent application No. 0180824—Mpock. Mechanical components spin in the solution and periodically raise out of the blood. Clots form on the spinning arms and are detected optically.

U.S. Pat. No. 4,105,411—Biver. Handheld device which acts like a stopwatch with a built-in heater. Blood is in test tubes and the blood flows back and forth across an open window. The user visually looks for clots.

U.S. Pat. No. 4,125,327—Margolis. Plunger-type device that can add compounds into whatever solution one is measuring. Reaction changes are measured optically.

U.S. Pat. No. 4,876,069—Jochimsen. Metal stirrer or ball in the blood that creates turbidity. Clotting time is measured by measuring turbidity optically.

U.S. Pat. No. 4,964,728—Kloth et al. Describes similar mechanisms to U.S. Pat. No. 4,876,069.

U.S. Pat. No. 5,167,145—Butler et al. Uses infrared to measure composition changes in the blood as it clots.

U.S. Pat. No. 6,555,064—Baugh et al. Benchtop device that sends a plunger into a test-tube with blood in it. Clotting is measured by the rate of descent of the plunger.

U.S. Pat. No. 6,438,498—Opalsky et al., Measures chemical composition of the clots as they flow across a channel. Uses conductivity and amperometric sensors to measure composition.

SUMMARY OF THE INVENTION

An object of the present invention is to provide a microsystem for determining clotting time of blood and a low-cost, single-use device for use therein wherein the device has no moving parts or expensive optical sensors or magnets.

In carrying out the above object and other objects of the present invention, a microsystem for determining clotting time of blood is provided. The microsystem includes a single-use device including: a microfluidic channel formed in the device; inlet and outlet ports in fluid communication with the channel wherein the inlet port allows the introduction of blood into the channel and wherein the blood flows along a length of the channel; and a microsensor at least partially in fluid communication with the channel for sensing a property of the blood at various locations along the length of the channel and providing corresponding signals. The microsystem also includes a signal processor which processes the signals to obtain the clotting time.

The signal processor may include a circuit for processing the signals to obtain a stop signal which indicates that the blood is clotted.

Further in carrying out the above object and other objects of the present invention, a low-cost, single-use device for analyzing blood coagulation is provided. The device includes a microfluidic channel. Inlet and outlet ports are in fluid communication with the channel. The inlet port allows the introduction of blood into the channel, and the blood flows along a length of the channel. A microsensor is at least partially in fluid communication with the channel for sensing a property of the blood at various locations along the length of the channel and providing corresponding signals.

The microsensor may include a pair of spaced, conductive traces extending along the length of the channel.

The conductive traces may be equally spaced or variably spaced along the length of the channel.

At least one of the conductive traces may be segmented at predetermined intervals along the length of the channel.

The conductive traces may be conductive metal or carbon traces.

The channel may be spiral-shaped to minimize footprint size of the device.

The microsensor may be spiral-shaped or may be spoke-shaped.

The property of the blood may be at least one of impedance and capacitance of the blood in the channel.

The conductive traces may include Ag/AgCl, gold, platinum or iridium lines at least partially disposed in the channel.

The microsensor may include a set of spaced conductors disposed in the channel adjacent the inlet port to provide a start signal when the blood is first introduced into the channel.

The device may further include a substrate and a cap including the inlet port. The channel is disposed between the cap and the substrate.

The blood may flow in the channel by either capillary action or laminar flow.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIGS. 1a-1d are side, sectional schematic views illustrating a typical microchannel processing sequence; FIG. 1a shows a starting substrate; FIG. 1b shows Ag sputtering and patterning with liftoff; FIG. 1c shows spinning and patterning of SU-8; FIG. 1d shows bonding of a glass cap and etching of openings to the channel;

FIG. 2 is a schematic perspective view of a unit-length of a portion of a microchannel with a pair of spaced conductive traces of the present invention;

DETAILED DESCRIPTION OF THE PREFERRED EMBODIMENTS

Figure 3:
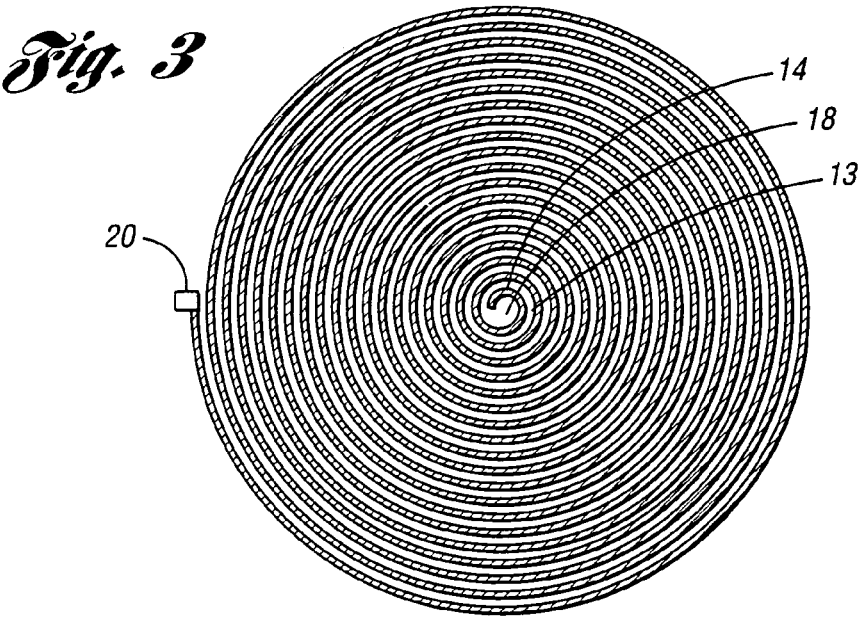
FIG. 3 is a top, sectional schematic view showing the lay out of a spiral-shaped microchannel of the present invention.

A microsystem and an inexpensive, disposable device for use in the microsystem capable of performing blood clotting tests at a patient's home or bedside are provided. The device generally includes a microchannel and a detection sensor. A small amount of blood is dispensed into the channel where capillary action and pressure differentials cause the blood to flow down the length of the channel. As clotting occurs, the blood will stop flowing and a determination that the blood has stopped traveling down the channel can be made by the sensor. The sensor can be, but is not limited to, an impedance sensor, a capacitance sensor, or a digital switch readout. The stop time is recorded and by taking the difference between the start time and stop time of the test, the clotting time of the blood can be determined.

The device may be fabricated by any number of techniques including, but not limited to, thin-film processing, injection molding, or lamination technologies.

Microfluidic Channel

As discussed above, the microfluidic channel can be fabricated in any number of cost-effective ways. One method of fabrication using thin-film processing techniques is discussed as an example. FIGS. 1a-1d are diagrams of the processing steps involved in forming the device. First, a suitable substrate 10 is chosen (this can be silicon with oxide or other passivation films, glass, etc.), and the sensing metal 12 is patterned onto the substrate 10. Next, a channel 13 is formed using a photoset polymer 14 such as SU-8 or polyimide films. Finally, a glass cap 16 (or other suitable material) is attached to the top of the channel 13 and an inlet hole 18 and an outlet hole (shown at 20 in FIG. 3) are etched or drilled in the cap 16 to allow the blood into the channel 13. FIG. 2 shows a unit-length cross-section of the microchannel 13 with the spaced conductive or metal traces 12 therein.

Figure 4A:
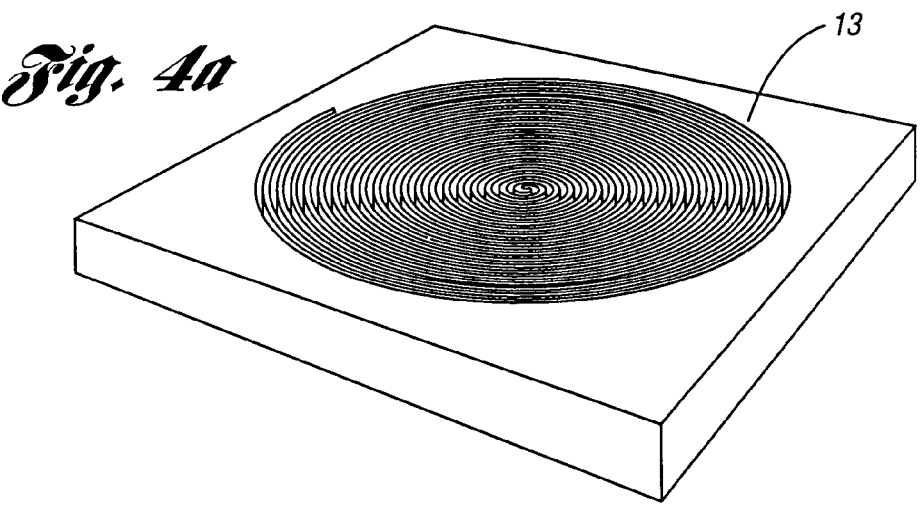
FIGS. 4a and 4b are perspective, schematic views (FIG. 4b being an enlarged view of a portion of FIG. 4a) of a layout of the spiral-shaped microchannel.
Figure 4B:
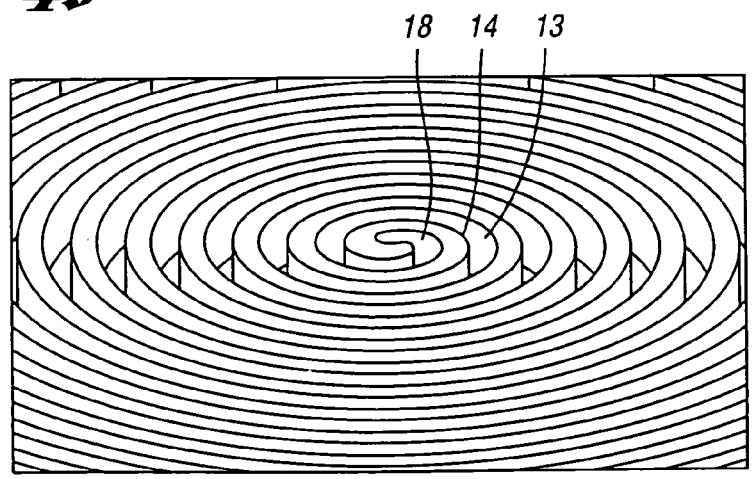

An example layout of the channel 13 is shown in FIG. 3. The channel 13 was laid out in a spiral to minimize the footprint size, but other configurations can be used if other design parameters are desired. FIGS. 4a and 4b show a 3D perspective of the channel 13 as drawn in a MEMCAD.

Sensor

Sensing the distance that the blood has traveled down the channel 13 can be achieved by a number of techniques. By placing the two parallel metal traces 12 throughout the length of the channel 13 (FIGS. 2 and 13a), a resistive or capacitive readout can be taken depending on the metal chosen. For example, if the blood has traveled a distance L(t), then the resistance seen between the two metal traces R(t) is:

$$R(t) = \frac{\rho}{z} \frac{w}{L(t)} \quad (1)$$

where ρ is the resistivity of blood, w is the separation between the metal lines 12, and z is the height of the channel 13. To increase the sensitivity of the device, the metal traces 12 can start some distance d into the channel 13 so that the effective distance traveled $L_{eff}(t)$ becomes L(t)-d and the impedance is given by:

$$R(t) = \frac{\rho}{z} \frac{w}{(L(t) - d)} \quad (2)$$

Another sensor example is a digital switch readout. Multiple pairs of traces (i.e., FIG. 13d) of metal can be placed at intervals throughout the length of the channel 13. As the blood flows past a certain metal trace pair, it will effectively "close the switch" indicating that the blood has reached that location. The switches can then be read out as a thermometer code indicating the distance the blood has traveled.

By monitoring the rate of change of resistance or capacitance, the clotting time can be determined. Similarly, by setting some conditions on the rate that consecutive digital switches must close, a clotting time can be determined with the digital switch technique. The timebase can be as simple as an operator with a stopwatch waiting for an indication from the device to stop the counter, or as complex as an integrated timing circuit with counters and digital readout detailing the clotting time.

It should also be noted that this device can incorporate other sensors into the channel 13 that might give useful information about the blood. For instance, ion-selective electrodes and voltammetric and temperature sensors could be added with only minimal changes to the device.

Microfluidic Channel

The following description is based on laminar flow rather than capillary flow. The blood may flow in the channel by either capillary action or laminar flow.

Figure 5:
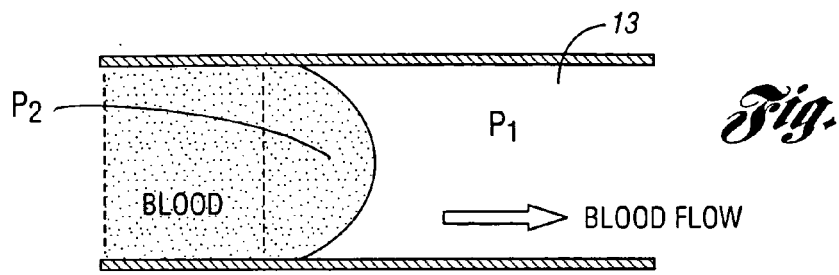
FIG. 5 is a side, sectional schematic view illustrating pressure differential in a laminar flow fluid.

As the blood begins to flow down the channel 13, it exhibits laminar flow characteristics (FIG. 5) and is governed by Laplace's Law:

$$\Delta P = P_2 - P_1 = \frac{4\sigma}{d_{cir}} \quad (3)$$

where P is the pressure, σ is the surface tension of the blood and $d_{cir}$ is the cross-sectional area of the channel 13 if it were a circular rather than rectangular channel and is given by:

$$d_{cir} = \frac{4 \times z}{x + z} \quad (4)$$

By conservation of mass, $$L(t)A = Q(L,t)t \quad (5)$$

where L(t) is the length the blood has flowed in time t, A is the cross-sectional area of the channel, and Q(L,t) is the volume flow rate of a liquid as a function of length and time. Poiseuille's Flow equation states that:

$$Q(L, t) = \frac{\pi \cdot \Delta P \cdot (d_{cir}/2)^4}{8 \cdot \eta(t) \cdot L(t)}. \quad (6)$$

where η(t) is the viscosity of the blood versus time. Differentiating (5) yields:

$$A\frac{\partial L}{\partial t} = Q(L, t) + t\frac{\partial Q(L, t)}{\partial t} \quad (7)$$

and further substitution yields, $$\left(\frac{16A}{\pi \Delta P(d_{cir}/2)^4}\right) L\delta L = \left(\frac{1}{\eta} - \frac{t}{\eta^2}\frac{\partial \eta}{\partial t}\right)\partial t \quad (8)$$

Thus, for a constant, worst-case low viscosity, which indicates that the blood does not coagulate, $$L(t) = \sqrt{\frac{\pi \Delta P(d_{cir}/2)^4 t}{4 \cdot A\eta}} \quad (9)$$

where η(t) has been replaced by a constant viscosity, η. Equation (9) gives the maximum length of the blood in the channel 13 at any time.

Figure 6:
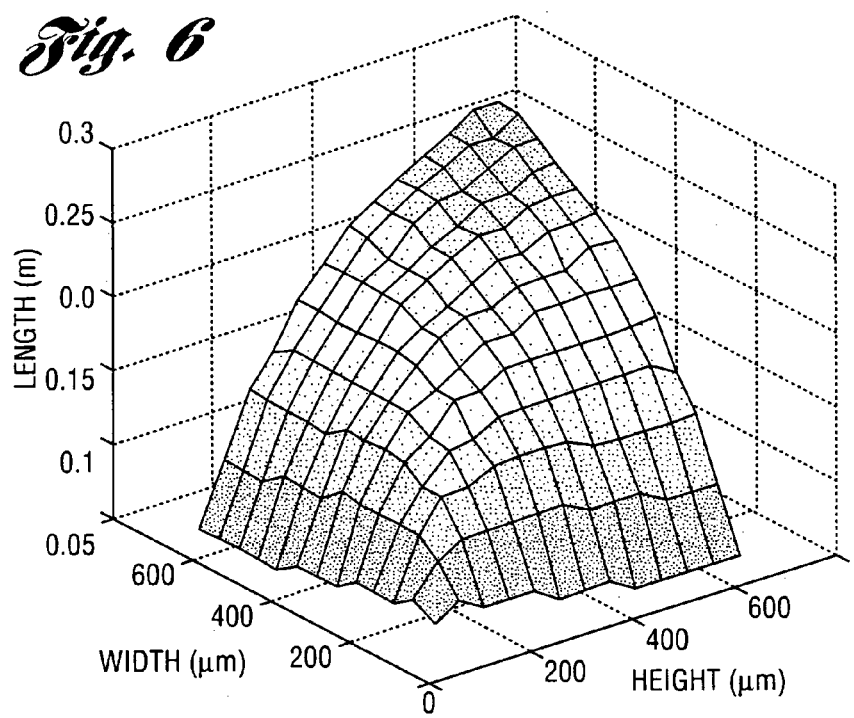
FIG. 6 is a 3D graph showing length of blood flow at a typical clotting time vs. channel width and height.

FIG. 6 is a plot of the length the blood travels down the channel as given by (9) at a typical clotting time versus channel dimensions. The plot shows various (x,z) pairs that yield a minimum channel length and thus, minimize die area and fabrication costs. Based on this information, the width, x, was chosen to be 50 μm to minimize layout area yet still be wide enough to let blood flow unimpeded. The corresponding height, z, is 450 μm, and the necessary channel length is 100 mm.

Figure 7:
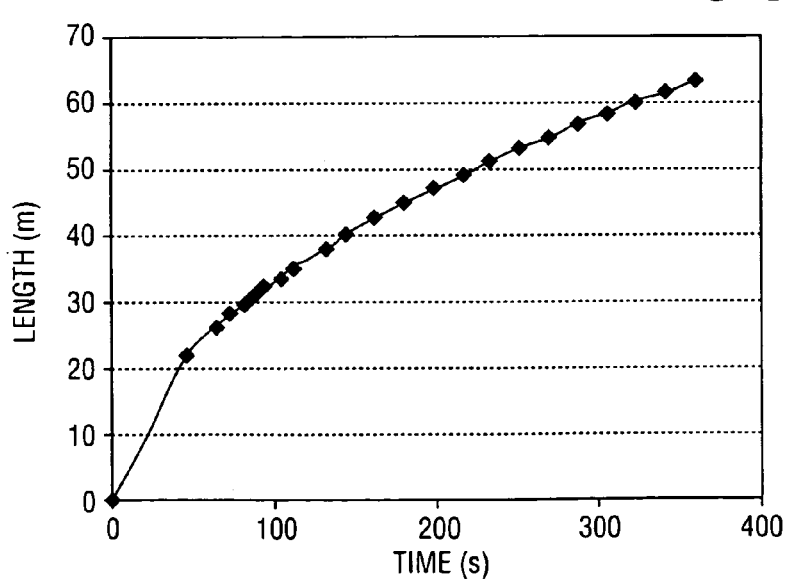
FIG. 7 is a graph of length of non-clotting blood (i.e., non-coagulating blood flow) vs. time.

FIG. 7 shows a plot of blood flow for non-coagulating blood vs. time for these values of x and z. The data is plotted through 300 seconds which is four times as long as will typically be needed for a clotting test.

Figure 8:
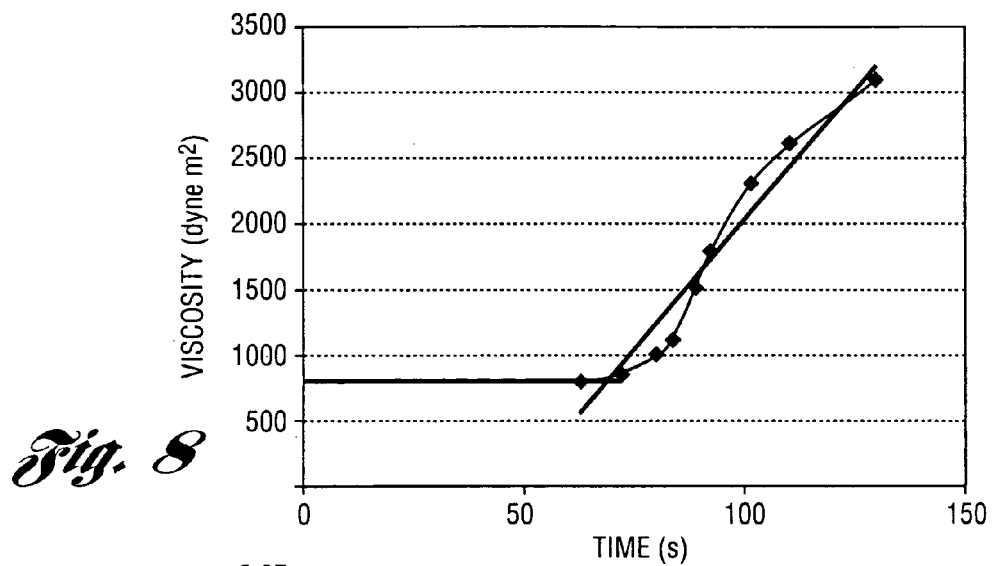
FIG. 8 is a graph of viscosity vs. time which illustrates a piecewise linear approximation of viscosity.

Determining the length of the blood flow during coagulation requires that the time-dependent viscosity be used in (7). To simplify the integration of the differential equation, a piecewise linear approximation of the changing viscosity was used (FIG. 8). The formula is:

$$\eta(t) = \begin{cases} 800 & \text{for } t < 72\,s \\ 38.8t - 1906 & \text{for } t \geq 72\,s \end{cases} \quad (10)$$

Thus, solving (9) yields, $$L(t) = C_1 \sqrt{\int_0^t \left(\frac{1}{\eta(t)} - \frac{t}{\eta^2}\frac{\partial \eta}{\partial t}\right)\partial t} \text{ or} \quad (11)$$

$$L(t) = \begin{cases} C_1 \sqrt{\int_0^t \frac{1}{800}\partial t} & \text{for } t \leq 72\,s \\ C_1 \sqrt{\int_0^{72} \frac{1}{800}\partial t + \int_{72}^t \frac{1906}{38.8t - 1906^2}\partial t} & \text{for } t > 72\,s \end{cases} \quad (12)$$

where $C_1$ is constant.

Figure 9:
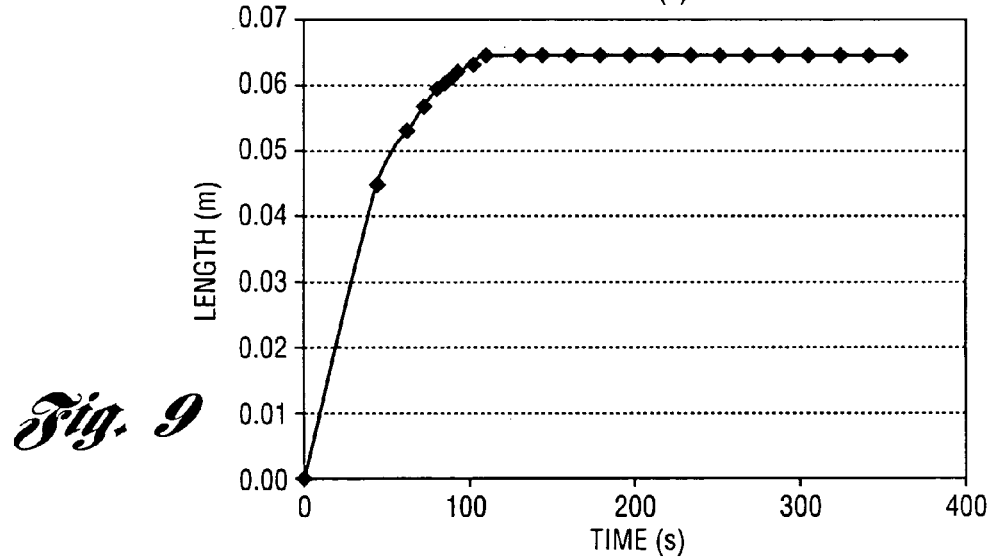
FIG. 9 is a graph of length of clotting blood (i.e., coagulating blood flow) vs. time.

The plot of blood flow during coagulation versus time is shown in FIG. 9. By comparing FIG. 7 and FIG. 9, it can be seen that the clotting blood travels a significantly shorter distance than the non-coagulating blood.

Sensor Example (Impedance)

Normally, a double-layer capacitance exists between a metal electrode and an ionic solution such as blood forming a polarized interface [10]. Ag/AgCl, in contrast, has the ability to exchange ions with the solution forming an ohmic connection between the electrode and the solution. The clotting time is measured by examining the varying resistance between the Ag/AgCl lines (spaced 30 μm apart, for example in FIG. 2) on the channel floor as the blood travels down the channel 13. However, it is to be understood that gold, platinum or iridium lines would be most likely used for capacitive readout. Also, carbon or other conductive materials could be used.

Like the surface tension of blood, the conductivity changes with respect to time as it clots [11], but this changing conductivity occurs after blood flow has stopped. Thus, a standard value for resistivity of blood, ρ=150 Ω/cm [12], was used in these calculations.

The value of resistance at a time, t, is given by:

$$R(t) = \frac{\rho}{z}\frac{w}{L(t)} \quad (13)$$

This, however, yields a very small ΔR when the distance of the blood flow is greater than 60 mm. Since this is the distance of blood flow for a typical clotting time test, the Ag/AgCl lines 12 that measure the impedance are started 40 mm away from the opening where the blood is initially dispensed. Thus, the resistance becomes, $$R(t) = \frac{\rho}{z}\frac{w}{(L(t) - 0.04)} \quad (14)$$

Figure 10:
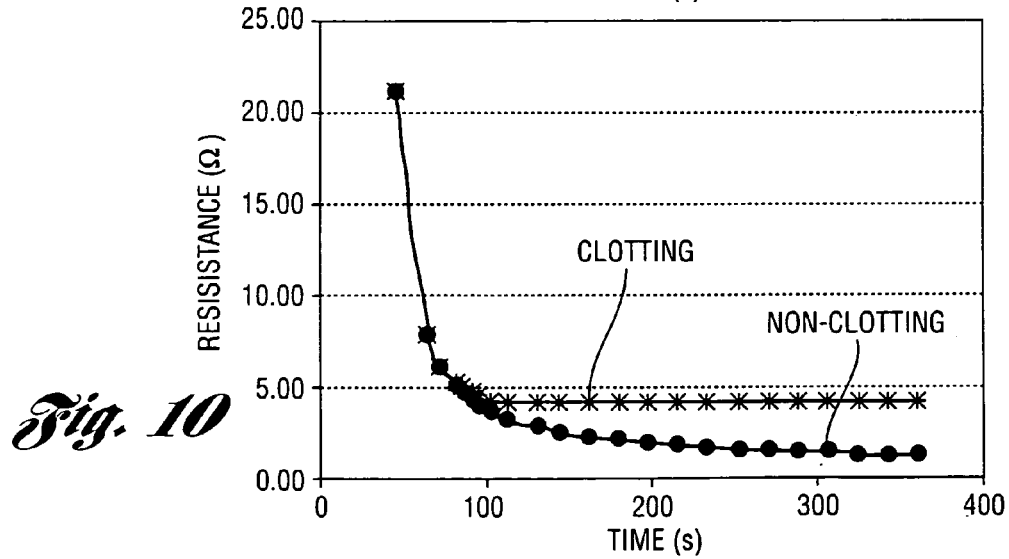
FIG. 10 is a graph of resistance of blood vs. time.

The data generated by (14) for both clotting, and non-clotting blood is presented in FIG. 10. From the plot, the resistance seen across the blood at the nominal clotting distance is around 4 Ω. A second set of Ag/AgCl lines 12 are placed directly under the blood inlet. These lines 12 give an instantaneous change in resistance as the blood is first injected to indicate the ACT test has started.

Figure 11:
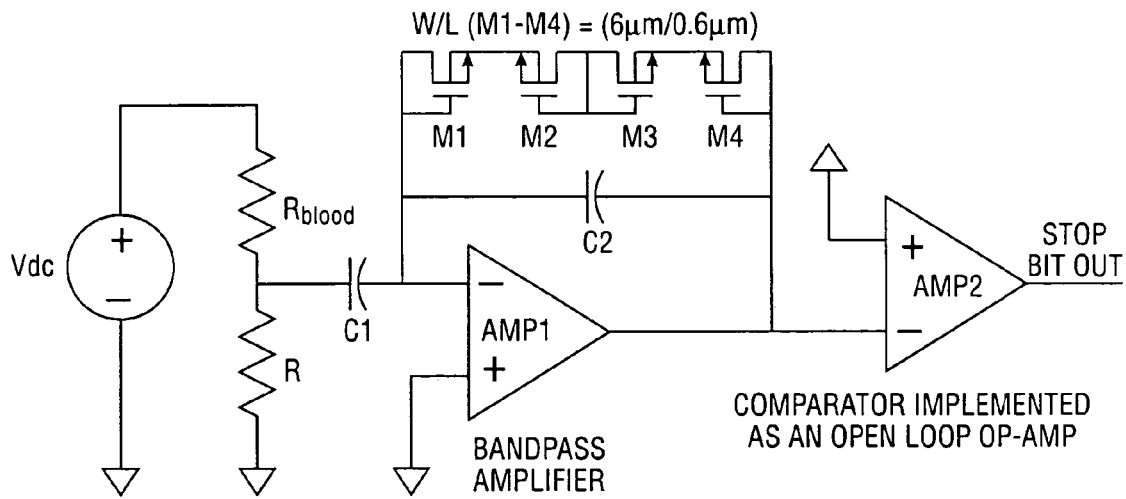
FIG. 11 is a schematic view of interface electronics for stop signal generation.

FIG. 11 shows an example readout circuit that can measure impedance. However, it is to be understood that any number of different circuit topologies could be used. When the blood is first inserted into the channel 13, a start signal is generated. Once the blood flow has traveled 40 mm into the channel 13, the resistance, $R_{blood}$, begins to change as shown in FIG. 10. This changes the voltage at the input of the amplifier, Amp1. The feedback configuration around Amp1 has a bandpass response set by the two capacitors, C1 and C2, and the diode connected transistors, M1-M4 [13]. Thus, Amp1 only has gain while $R_{blood}$ is changing. This gain drives the output of the comparator, Amp2, to a logic high. When $R_{blood}$ stops changing because the blood has clotted, the output of the amplifier will go to zero volts and the comparator output will go to a logic low. The low-frequency pole of the bandpass response enables detection of slow changing impedances but does not pass any DC impedance values. Thus, the output bit is driven low when the rate of change of resistance drops below a certain level. This indicates that clotting has occurred, and the clotting time can be calculated as the time difference between the positive edge of the start signal and the negative edge of the stop signal.

Figure 12:
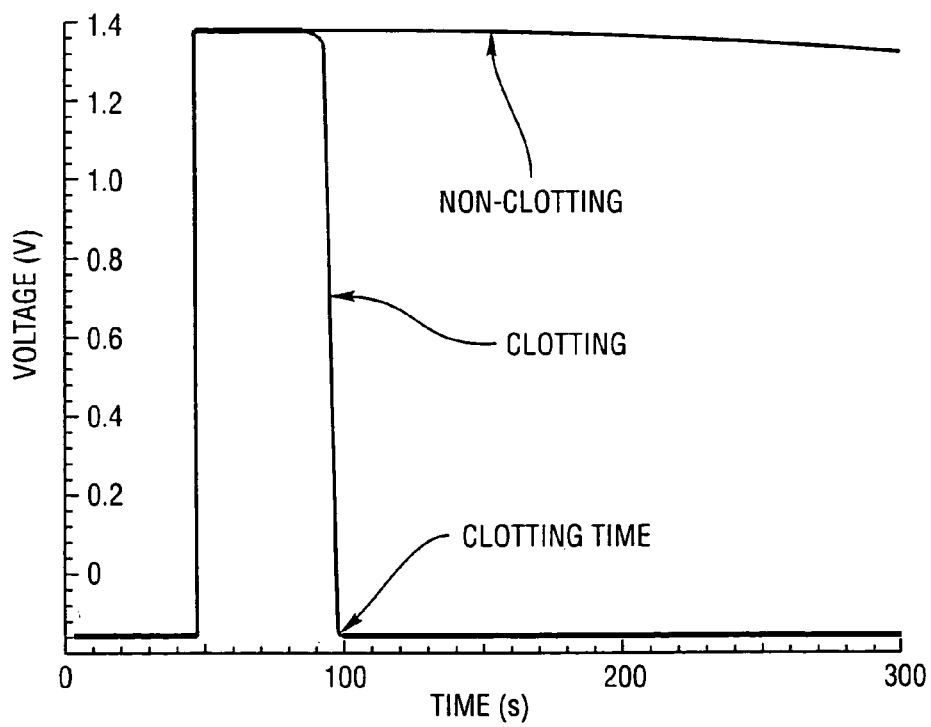
FIG. 12 is a graph of stop signal vs. time for clotting and non-clotting blood.

The readout circuitry was simulated using SPECTRE by Cadence Designs. SPECTRE, through its Analog-HDL interface, allowed the programming of the resistor, $R_{blood}$, to mimic the resistance changes as blood flowed down the channel according to FIG. 10. FIG. 12 shows the output of the readout circuitry for both clotting and non-clotting blood.

FIGS. 13a-13h show a number of possible electrode configurations for the microsensor. The different electrode configurations can be intermixed or combined.

Figure 13A:
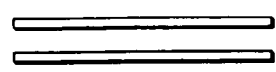
FIGS. 13a-13h are schematic views of various electrode configurations wherein FIGS. 13g and 13h also show two possible microchannel configurations.

FIG. 13a shows two parallel electrodes which could traverse the length of the channel 13. The distance blood flows is measured through an analog impedance change.

Figure 13B:
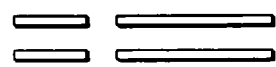

FIG. 13b shows two sets of parallel electrodes down the length of the channel. The first set acts as a digital "start" bit when blood first hits them, immediately shorting them out electrically.

Figure 13C:

FIG. 13c shows multiple sections of parallel electrodes used to measure the analog impedance change with greater resolution.

Figure 13D:
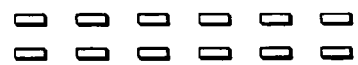

FIG. 13d shows many short electrodes which are electrically shorted together when the blood reaches them. Data is read out digitally like watching switches close.

Figure 13E:

FIG. 13e shows one continuous reference electrode to reduce pin count. The other electrodes can be read digitally or by an analog impedance method. This method can be extended to all of the electrode configurations presented herein.

Figure 13F:
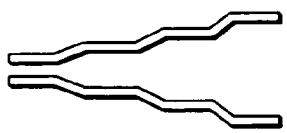

FIG. 13f shows that the electrodes can have changing separations to help increase the resolution of the impedance measurement at long blood flow distances.

At this point, it is important to note that readout can use resistance, capacitance, or combination measurements.

Figure 13G:
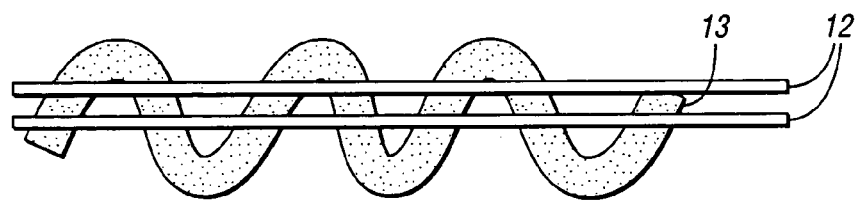

FIG. 13g shows that the electrodes 12 can intersect the channel 13. This creates step-size resistance changes.

Figure 13H:
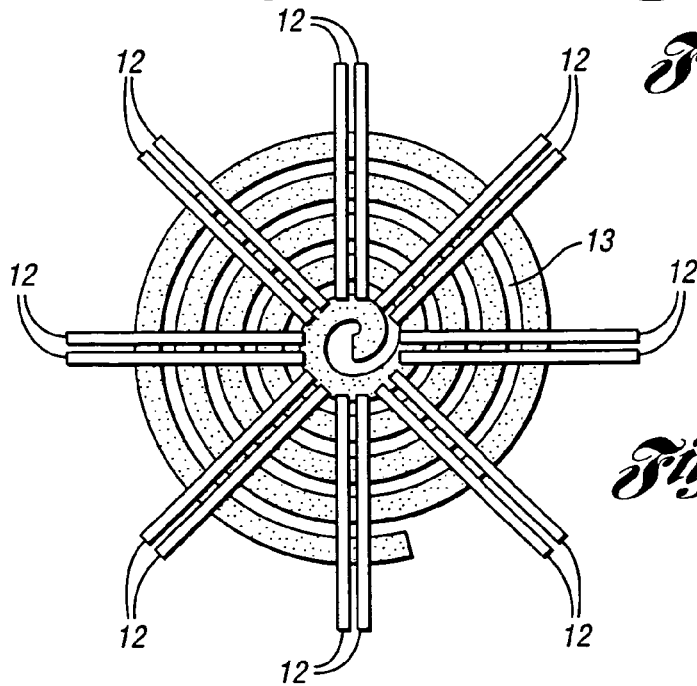

FIG. 13h shows that the electrodes 12 can form a kind of spoke design with the spiral channel 13. The electrodes 12 can be in pairs or they can share a common "reference" electrode.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A microsystem for determining clotting time of blood, the microsystem comprising:
a single-use device including: a microfluidic channel formed in the device; inlet and outlet ports in fluid communication with the channel wherein the inlet port allows the introduction of blood into the channel and wherein the blood flows along a length of the channel; and a microsensor at least partially in fluid communication with the channel for sensing a property of the blood at various locations along the length of the channel and providing corresponding signals wherein the microsensor includes a pair of spaced, conductive traces extending along the length of the channel and wherein the conductive traces are variably spaced along the length of the channel; and
a signal processor for processing the signals to obtain the clotting time.

2. The microsystem as claimed in claim 1, wherein at least one of the conductive traces is segmented at predetermined intervals along the length of the channel.

3. The microsystem as claimed in claim 1, wherein the conductive traces are conductive metal or carbon traces.

4. The microsystem as claimed in claim 1, wherein the channel is spiral-shaped to minimize footprint size of the device.

5. The microsystem as claimed in claim 4, wherein the microsensor is also spiral-shaped.

6. The microsystem as claimed in claim 4, wherein the microsensor is spoke-shaped.

7. The microsystem as claimed in claim 1 wherein the signal processor includes a circuit for processing the signals to obtain a stop signal which indicates that the blood is clotted.

8. The microsystem as claimed in claim 1, wherein the property of the blood is at least one of impedance and capacitance of the blood in the channel.

9. The microsystem as claimed in claim 1, wherein the conductive traces includes Ag/AgCl, gold, platinum or iridium lines at least partially disposed in the channel.

10. The microsystem as claimed in claim 1, wherein the microsensor additionally includes a set of spaced conductors disposed in the channel adjacent the inlet port to provide a start signal when the blood is first introduced into the channel and wherein the signal processor processes the start signal.

11. The microsystem as claimed in claim 1, wherein the device further includes a substrate and a cap having the inlet port, the channel being disposed between the cap and the substrate.

12. The microsystem as claimed in claim 1, wherein the blood flows in the channel by capillary action or laminar flow.

13. A low-cost, single-use device for analyzing blood coagulation, the device comprising:
a microfluidic channel;
inlet and outlet ports in fluid communication with the channel wherein the inlet port allows the introduction of blood into the channel and wherein the blood flows along a length of the channel; and
a microsensor at least partially in fluid communication with the channel for sensing a property of the blood at various locations along the length of the channel and providing corresponding signals wherein the microsensor includes a pair of spaced, conductive traces extending along the length of the channel and wherein the conductive traces are variably spaced along the length of the channel.

14. The device as claimed in claim 13, wherein at least one of the conductive traces is segmented at predetermined intervals along the length of the channel.

15. The device as claimed in claim 13, wherein the conductive traces are conductive metal or carbon traces.

16. The device as claimed in claim 13, wherein the channel is spiral-shaped to minimize footprint size of the device.

17. The device as claimed in claim 16, wherein the microsensor is also spiral-shaped.

18. The device as claimed in claim 16, wherein the microsensor is spoke-shaped.

19. The device as claimed in claim 13, wherein the property of the blood is at least one of impedance and capacitance of the blood in the channel.

20. The device as claimed in claim 13, wherein the conductive traces includes Ag/AgCl, gold, platinum or iridium lines at least partially disposed in the channel.

21. The device as claimed in claim 13, wherein the microsensor additionally includes a set of spaced conductors disposed in the channel adjacent the inlet port to provide a start signal when the blood is first introduced into the channel.

22. The device as claimed in claim 13, further comprising a substrate and a cap including the inlet port, the channel being disposed between the cap and the substrate.

23. The device as claimed in claim 13, wherein the blood flows in the channel by capillary action or laminar flow.

* * * * *